United States Patent [19]
Darnell

[11] Patent Number: 5,356,291
[45] Date of Patent: Oct. 18, 1994

[54] TREATMENT OF A TOOTH

[75] Inventor: Daniel H. Darnell, Hanceville, Ala.

[73] Assignee: Dunhall Pharmaceuticals, Inc., Gravette, Ark.

[21] Appl. No.: 9,355

[22] Filed: Jan. 26, 1993

Related U.S. Application Data

[63] Continuation of Ser. No. 793,244, Nov. 12, 1991, abandoned, which is a continuation of Ser. No. 612,599, Nov. 5, 1990, abandoned, which is a continuation-in-part of Ser. No. 374,985, Jul. 3, 1989, Pat. No. 4,968,251.

[51] Int. Cl.$^5$ .............................. A61C 15/00
[52] U.S. Cl. ........................ 433/216; 433/80
[58] Field of Search ............ 433/215, 216, 217.1, 433/136, 80, 229; 604/77; 128/861

[56] References Cited

U.S. PATENT DOCUMENTS

| | | | |
|---|---|---|---|
| 3,527,219 | 9/1970 | Greenberg | 433/215 |
| 3,624,909 | 12/1971 | Greenberg | 433/80 |
| 4,138,814 | 2/1979 | Weitzman | 433/215 |
| 4,376,628 | 3/1983 | Aardse | 433/80 |
| 4,428,373 | 1/1984 | Seid et al. | 433/80 |
| 4,544,354 | 10/1985 | Gores et al. | 433/80 |
| 4,968,251 | 11/1990 | Darnell | 433/80 |
| 4,983,381 | 1/1991 | Torres Zaragoza | 433/215 |
| 5,009,885 | 4/1991 | Yarborough | 433/215 |

FOREIGN PATENT DOCUMENTS 2002637  2/1979  United Kingdom ............... 433/215

*Primary Examiner*—Cary E. O'Connor
*Attorney, Agent, or Firm*—Boyd D. Cox

[57] ABSTRACT

An apparatus and method is disclosed for treating a tooth with an active agent such as a tooth whitening agent comprising a stint having an internal region defined by an internal surface. A plurality of indentations are formed in the internal surface for retaining the active agent to maintain the active agent in contact with the tooth when the stint is applied upon the tooth. The stint is molded from a sheet of plastic material with the indentations being formed by an abrading process such as abrasive blasting or the like.

42 Claims, 6 Drawing Sheets

TREATMENT OF A TOOTH

This is a continuation of copending application Ser. No. 07/793,244, filed on Nov. 12, 1991, now abandoned; which is a continuation of Ser. No. 612,599, filed Nov. 5, 1990, now abandoned; which is a continuation-in-part of Ser. No. 374,985, filed Jul. 3, 1989, now U.S. Pat. No. 4,985,251.

BACKGROUND OF THE INVENTION

1. Field Of The Invention

This invention relates to medicine and dentistry and more particularly to an improved method and apparatus for applying an active agent to the surface of a tooth and/or other oral structures.

2. Prior Art Statement

The prior art has known many devices and methods for externally treating a tooth or teeth of a patient. The most primitive method of externally treating a tooth involves the direct application of an active agent to the tooth of the patient. Examples of the external treatment of a tooth includes the direct application of active agents such as fluoride, tooth whiteners, antibiotics, antihistamines and topical anesthetics.

Although the external treatment of a tooth by the direct application of an active agent has achieved some success, several problems exist with this method. First, the direct application of an active agent is generally inefficient since the active agent can be applied to the surface of the tooth for only a relatively short period of time. The relatively short period of time of application is determined by the length of time the active agent remains on the tooth of the patient. The length of time the active agent remains on the tooth of the patient is generally determined by the viscosity of the active agent and the ability of the active agent to remain on the tooth as well as the ability of the patient to remain immobile during the treatment.

In an effort to overcome these problems, some in the prior art have increased the concentration of the active agent in an effort to produce satisfactory results within the limited period of time permitted by the direct application of the active agent. Unfortunately, the increase in the concentration of the active agent produces undesirable side effects for the patient.

Others in the prior art have utilized a plastic stint molded to overlay the teeth of the patient in an effort to retain a tooth whitening agent in contact with the teeth of a patient over an extended period of time. Such a method is set forth in an article entitled "Nightguard Vital Bleaching" which has been published in *Quintessence International*, Volume 20, March, 1989. In this method a stint is molded to fit the entire upper or lower teeth of the patient and to seal with the gingiva of the patient. The active agent is introduced into the stint, and the stint is inserted upon the teeth of the patient to retain the active agent in intimate contact with the teeth of the patient.

Although the use of a plastic stint allowed the active agent to remain in contact with the tooth for an extended period of time, the use of the plastic stint had certain disadvantages. First, since the plastic stint was molded to intimately fit with the entire upper or lower teeth of the patient, the stint was uncomfortable due to the tightness of the fit with the teeth. Second, the stint sealed with the gingiva of the patient making the stint incapable of fitting with a single tooth or plural teeth, since such a stint could not properly seal with the gingiva of the patient. Third, the stint had to be cut back adjacent to the gingival margin to prevent undesired deterioration of the gingiva due to the intimate contact of the stint with the gingiva during the treatment process. Fourth, intimate fit of the stint with the entire upper or lower teeth of the patient prevented ingress and egress of oxygen to the internal region of the stint. Fifth, intimate fit of the stint with the entire upper or lower teeth of the patient made the stint difficult to remove in some instances. Sixth, notwithstanding the intimate fit of the stint with the entire upper or lower teeth of the patient, the active agent within the internal region of the stint would over time migrate from the stint thus reducing the effectiveness of the active agent upon the teeth.

In my prior application Ser. No. 374,985 filed Jul. 3, 1989 now U.S. Pat. No. 4,968,251, a retaining material was interposed between the stint and the tooth. The retaining material acted as a reservoir and maintained the active agent in intimate contact with the tooth for a longer period of time than the whitening processes of the prior art. Furthermore, the retaining material could provide a preferential treatment of a selected portion of a tooth.

It is an object of the present invention to provide an improved method and apparatus for treating a tooth with an active agent which produces results which are superior to the results heretofore known to the art.

Another object of this invention is to provide an improved method and apparatus for treating a tooth with an active agent which is an alternate apparatus and method to my prior application Ser. No. 374,985 filed Jul. 3, 1989 now U.S. Pat. No. 4,968,251.

Another object of this invention is to provide an improved method and apparatus for treating a tooth with an active agent wherein a retaining means is disposed within the stint for maintaining the active agent against the surface of the tooth of the patient.

Another object of this invention is to provide an improved method and apparatus for treating a tooth with an active agent wherein a plurality of indentations are formed on an inner surface of the stint for providing baffles for the active agent to prevent the loss of the active agent from the stint.

Another object of this invention is to provide an improved method and apparatus for treating a tooth or other oral structures within the oral cavity with an active agent.

Another object of this invention is to provide an improved method and apparatus for treating a tooth with an active agent which is capable of fitting with a single tooth or a plurality of teeth of the patient.

Another object of this invention is to provide an improved method and apparatus for treating a tooth with an active agent wherein the stint may overlie the gingival margin without deterioration or irritation of the gingiva of the patient.

Another object of this invention is to provide an improved method and apparatus for treating a tooth with an active agent wherein the stint allows the ingress and egress of oxygen to the gingival tissue adjacent to the stint.

Another object of this invention is to provide an improved method and apparatus for treating a tooth with an active agent wherein the stint may be easily removed by the patient.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention within the scope of the invention. Accordingly other objects and a full understanding of the invention may be had by referring to the summary of the invention, the detailed description describing the preferred embodiment, in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved method of treating a tooth with an active agent, comprising the steps of making a model of the tooth and molding a stint to define an internal region to overlay the tooth. Indentations are formed within the internal region of the stint. The active agent is introduced into the stint prior to the stint being applied upon the tooth. The indentations maintain the active agent in contact with the tooth and provide a reservoir for excess quantities of the active agent.

In a more specific embodiment of the invention, the stint is vacuum formed from a sheet of plastic material over the model of the tooth or a plurality of teeth. The stint is trimmed to terminate at the juncture of the tooth and the gingiva tissue. The indentations are formed within the internal region of the stint by abrading an internal surface of the stint. Preferably, the indentations are formed by an abrasive blasting process after the completion of the molding of the stint. The stint seals the internal region from the external region of the stint proximate the termination of the stint at the juncture of the tooth and the gingiva tissue.

In one embodiment of the invention, the indentations are preferentially formed into selected portions of the internal surface of the stint to preferentially treat a portion of the tooth adjacent the indentations.

The foregoing has outlined rather broadly the more pertinent and important features of the present invention in order that the detailed description that follows may be better understood so that the present contribution to the art can be more fully appreciated. Additional features of the invention which form the subject of the claims of the invention will be described hereinafter. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 1A is a first step in the prior art process illustrating the positioning of a model of the teeth upon a vacuum table;

FIG. 1B is a second step in the prior art process illustrating the heating of a plastic material for forming the stint;

FIG. 1C is a third step in the prior art process illustrating the positioning of the heated plastic material upon the model;

FIG. 1D is a fourth step in the prior art process illustrating the vacuum forming of the heated plastic material upon the model to form the stint;

FIG. 1E is a fifth step in the prior art process illustrating the removal of the vacuum formed stint from the model and the trimming of the vacuum formed stint;

FIG. 1F is a seventh step in the prior art process illustrating the introduction of the active agent within the stint;

FIG. 2A is a first step in the first embodiment of the present invention illustrating the positioning of a model of the teeth upon a vacuum table;

FIG. 2B is a second step in the first embodiment of the present invention illustrating a sheet of a retaining material positioned upon the model of the teeth and the heating of a plastic material for forming the stint;

FIG. 2C is a third step in the first embodiment of the present invention illustrating the positioning of the heated plastic material upon the model with the retaining material interposed therebetween;

FIG. 2D is a fourth step in the first embodiment of the present invention illustrating the vacuum forming of the heated plastic material and the retaining material upon the model to form the stint;

FIG. 2E is a fifth step in the first embodiment of the present invention illustrating the removal of the vacuum formed stint from the model and the trimming of the vacuum formed stint and the retaining material;

FIG. 2F is a sixth step in the first embodiment of the present invention illustrating the introduction of the active agent within the retaining material within the stint;

FIG. 3A is a first step in the second embodiment of the present invention illustrating the positioning of a model of the teeth upon a vacuum table;

FIG. 3B is a second step in the second embodiment of the present invention illustrating the heating of a plastic material for forming the stint;

FIG. 3C is a third step in the second embodiment of the present invention illustrating the positioning of the heated plastic material upon the model;

FIG. 3D is a fourth step in the second embodiment of the present invention illustrating the vacuum forming of the heated plastic material upon the model to form the stint;

FIG. 3E is a fifth step in the second embodiment of the present invention illustrating the removal of the vacuum formed stint from the model and the trimming of the vacuum formed stint;

FIG. 3F is a sixth step in the second embodiment of the present invention illustrating the positioning of a retaining material upon the model;

FIG. 3G is a seventh step in the second embodiment of the present invention illustrating the forming of the retaining material upon the model by the formed stint;

FIG. 3H is an eighth step in the second embodiment of the present invention illustrating the trimming of the retaining material to the stint;

FIG. 8A is a first step in the third embodiment of the present invention illustrating the positioning of a model of the teeth upon a vacuum table;

FIG. 8B is a second step in the third embodiment of the present invention illustrating the heating of a plastic material for forming the stint;

FIG. 8C is a third step in the third embodiment of the present invention illustrating the positioning of the heated plastic material upon the model;

FIG. 8D is a fourth step in the third embodiment of the present invention illustrating the vacuum forming of the heated plastic material upon the model to form the stint;

FIG. 8E is a fifth step in the third embodiment of the present invention illustrating the removal of the vacuum formed stint from the model and the trimming of the vacuum formed stint;

FIG. 8F is a sixth step in the third embodiment of the present invention illustrating the abrading of an internal region of the stint;

FIG. 8G is a seventh step in the third embodiment of the present invention illustrating the cleaning of an internal region of the stint;

FIG. 8H is an eighth step in the third embodiment of the present invention illustrating the introduction of the active agent within the stint;

Similar reference characters refer to similar parts throughout the several Figures of the drawings.

DETAILED DISCUSSION

Figure 1A:
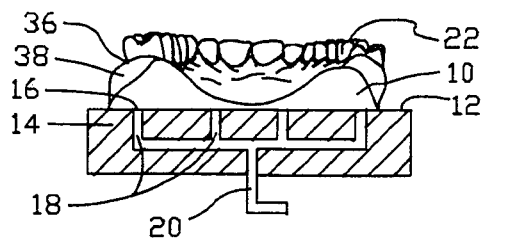
FIGS. 1A-1F are rear views partially in section of the prior art process of treating a tooth with a stint with FIGS. 1A-1F illustrating the individual process steps.

FIGS. 1A-1F illustrate a method of whitening a tooth with an active agent in accordance with the teaching of the prior art such as the prior art article "Nightguard Vital Bleaching" (*Quintessence International*, volume 20, March, 1989). FIG. 1A is a first step in the prior art process illustrating the positioning of a model 10 upon an upper surface 12 of a vacuum table 14. The vacuum table 14 defines a plurality of apertures 16 which are connected by conduits 18 to a manifold 20. The manifold 20 is connected to a source of vacuum (not shown). A model 10 is a reproduction of the teeth 22 of a patient and is constructed in a conventional manner as should be well known to those skilled in the art. The model 10 is positioned upon the upper surface 12 of the vacuum table 14 as shown.

Figure 1B:
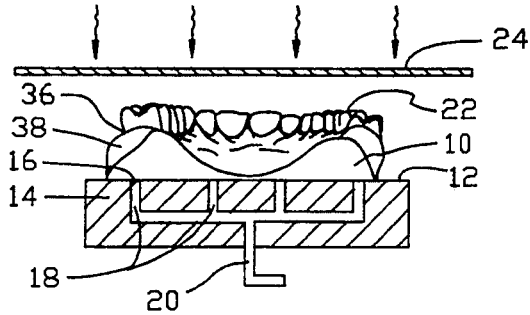

FIG. 1B is a second step in the prior art process illustrating the heating of a sheet plastic material 24 for forming a stint 30.

Figure 1C:
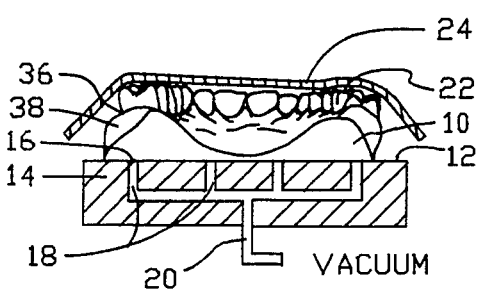

FIG. 1C is a third step in the prior art process illustrating the positioning of the heated sheet of plastic material 24 upon the model 10. The heated sheet of plastic material 24 begins to form into the contour of the model 10 by the action of gravity.

Figure 1D:
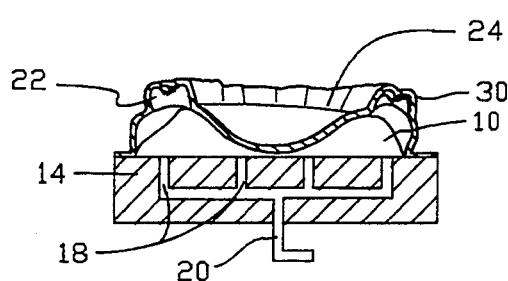

FIG. 1D is a fourth step in the prior art process illustrating the application of a vacuum to the manifold 20 for vacuum forming of the heated plastic material 24 upon the model 10 to form the stint 30. The vacuum forming process forms the heated plastic material 24 into an exact reproduction of the outer surfaces of the teeth 22 of the patient.

Figure 1E:
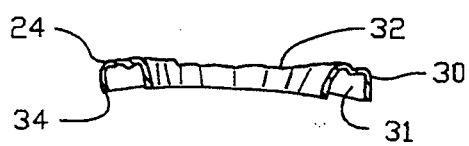

FIG. 1E is a fifth step in the prior art process illustrating the removal of the stint 30 from the model 10. The stint 30 is formed with an internal region 31 and an external region 32. The stint 30 is trimmed by a cutting tool (not shown) such as crown scissors to terminate at 34 proximate the junction 36 of the teeth 22 and the gingival tissue 38 commonly referred to as the tooth gingival margin.

Figure 1F:
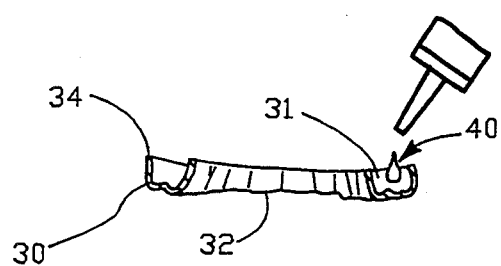

FIG. 1F is a seventh step in the prior art process illustrating the introduction of the active agent 40 within the internal region 31 of the stint 30. The prior art has used this process for whitening teeth through the use of a nonaqueous oral peroxy compound as an active agent. After the active agent is applied, the stint 30 containing the active agent 40 is applied upon the teeth 22 of the patient. The termination 34 of the stint 30 seals with the gingiva 38 to retain the active agent 40 within the internal region 31 of the stint 30.

Figure 2A:
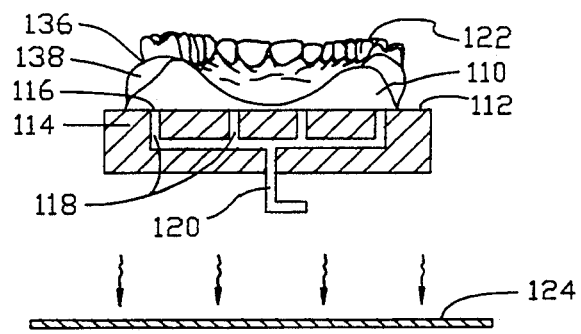
FIGS. 2A-2F are rear views partially in section of a first embodiment of the present invention for treating a tooth with a stint with FIGS. 2A-2F illustrating the individual process steps.

FIGS. 2A-2F are rear views partially in section of a first embodiment of the present invention for treating a tooth with a stint and with FIGS. 2A-2F illustrating the individual process steps. FIG. 2A is a first step in the first embodiment of the present invention illustrating the positioning of a model 110 upon an upper surface 112 of a vacuum table 114. The vacuum table 114 defines a plurality of apertures 116 which are connected by conduits 118 to a manifold 120 for connection to a source of vacuum (not shown). A model 110 is a reproduction of the teeth 122 of a patient and is constructed in a conventional manner. The model 110 is positioned upon the upper surface 112 of the vacuum table 114 as shown.

In contrast to the prior art process shown in FIGS. 1A-1F, a retaining material 126 is positioned upon the model 110. The retaining material in this embodiment is shown as a close cell foam material such as low density foamed polyethylene having a thickness of 1/32" to 3/32". The retaining material 126 possesses a natural resiliency as well as non uniform outer surfaces which are desirable for the practice of the present invention.

Figure 2B:
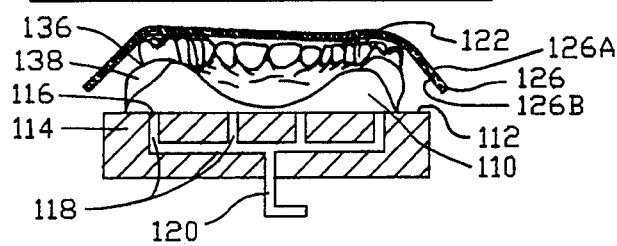

FIG. 2B is a second step in the first embodiment of the present invention illustrating the heating of a plastic material 124 for forming the stint 130. The plastic material 124 for the stint 130 is again selected to be easily formed at moderate temperatures such as 0.020 inch thickness polycarbonate. Preferably, the melting temperature of the retaining material 126 is less than the melting temperature of the plastic material 124 for the stint 130.

Figure 2C:
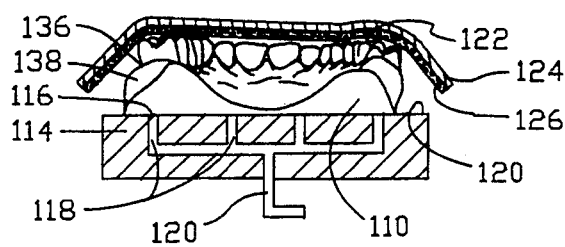

FIG. 2C is a third step in the first embodiment of the present invention illustrating the positioning of the heated sheet of plastic material 124 upon an inner surface 126A of the retaining material 126 while the retaining material 126 rests on the model 110. Since the melting temperature of the retaining material 126 is less than the melting temperature of the stint plastic material 124, the inner surface 126A of the retaining material 126 is heat fused to the plastic material 124.

Preferably, the melting temperature of the plastic material 124 for the stint 130 is selected to be higher than the melting temperature of the retaining material 126 to enable heat fusion of the inner surface 126A while being sufficiently low to prevent the destruction, melting or distortion of the interior or an outer surface 126B of the retaining material 126. Furthermore, only the inner surface 126A of the retaining material 126 is heat fused to the plastic material 124 for maintaining the resiliency of the resilient material 126.

After the heated sheet of plastic material 124 fuses with the retaining material 126, the sheet of plastic material 124 and the fused retaining material 126 begin to form into the contour of the model 110 by the action of gravity.

Figure 2D:
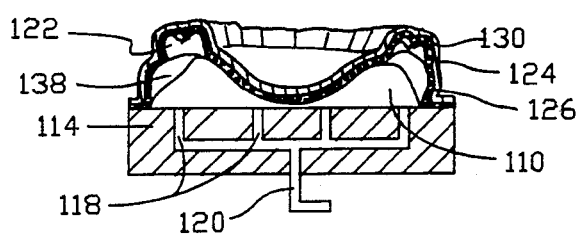

FIG. 2D is a fourth step in the first embodiment of the present invention illustrating the application of a vacuum to the manifold 120 for vacuum forming of the heated plastic material 124 and the interposed retaining material 126 upon the model 110 to form the stint 130. The vacuum forming process forms the heated plastic material 124 into a reproduction of the outer surfaces of the teeth 122 of the patient. However, in contrast to the prior art process, the internal region of the stint 130 is spaced from the outer surfaces of the teeth 122 of the patient by the thickness of the retaining material 126.

Figure 2E:
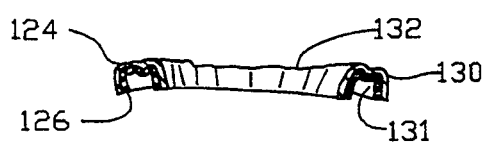

FIG. 2E is a fifth step in the first embodiment of the present invention illustrating the removal of the stint 130 from the model 110. The stint 130 is formed with an internal region 131 now defined by the retaining material 126 and an external region 132. The stint 130 is trimmed by a cutting tool (not shown) to terminate at 134 proximate the junction 136 of the teeth 122 and the gingiva tissue 138. As the stint 130 is trimmed, both the plastic material 124 and the retaining material 126 are simultaneously trimmed by the cutting tool.

Figure 2F:
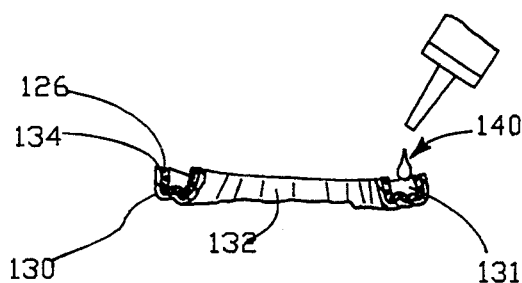

FIG. 2F is a sixth step in the first embodiment of the present invention illustrating the introduction of the active agent 140 within the internal region 131 of the stint 130. The presence of the retaining material 126 in the internal region 131 of the stint 130 aids in retaining the active agent 140 within the stint 130 and in close proximity to the teeth 122 of the patient to provide superior results relative to the prior art.

After the active agent 140 is introduced into the internal region 131 of the stint 130, the stint 130 is inserted over the teeth 122 of the patient. The non uniform surface of the retaining material 126 within the stint 130 provides baffles to retain the active agent 140 within the internal region 131 of the stint 130.

Figure 3A:
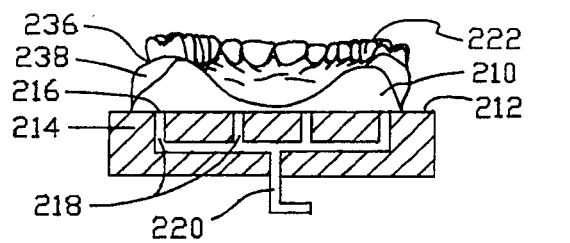
FIGS. 3A-3H are rear views partially in section of a second embodiment of the present invention for treating a tooth with a stint with FIGS. 3A-3H illustrating the individual process steps.

FIGS. 3A-3I are rear views partially in section of a second embodiment of the present invention for treating a tooth with a stint with FIGS. 3A-3I illustrating the individual process steps. FIG. 3A is a first step in the second embodiment of the present invention illustrating the positioning of a model 210 of the teeth 222 of a patient upon an upper surface 212 of a vacuum table 214 with the vacuum table 214 defining a plurality of apertures 216 which are connected by conduits 218 to a manifold 220 for connection to a source of vacuum (not shown).

Figure 3B:
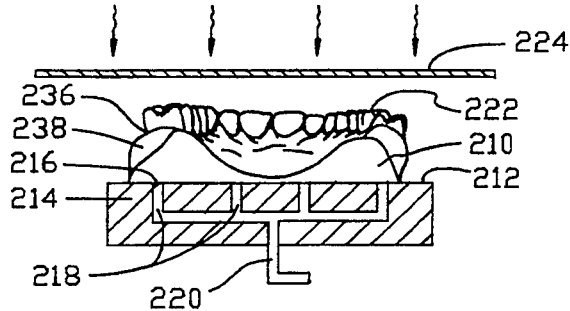

FIG. 3B is a second step in the second embodiment of the present invention illustrating the heating of a plastic material 224 for forming a stint 230. The plastic material 224 is again selected to be easily formed at moderate temperatures by conventional means.

Figure 3C:
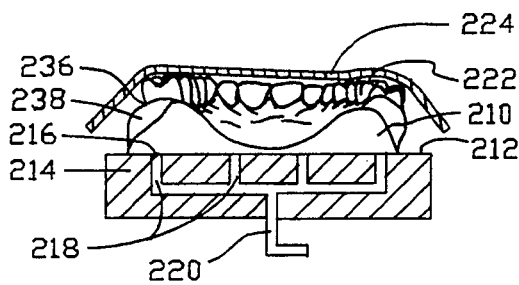

FIG. 3C is a third step in the second embodiment of the present invention illustrating the positioning of the heated plastic material 224 upon the model 210 with the heated sheet of plastic material 224 beginning to form into the contour of the model 210 by the action of gravity.

Figure 3D:
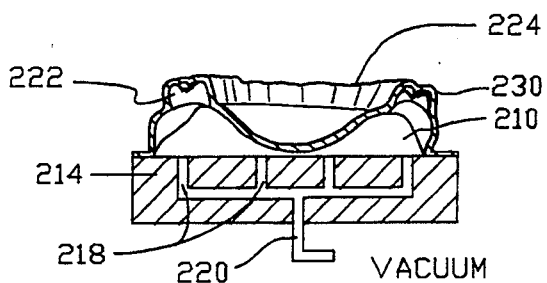

FIG. 3D is a fourth step in the second embodiment of the present invention illustrating the application of a vacuum to the manifold 220 for vacuum forming of the heated plastic material 224 upon the model 210 to form the stint 230.

Figure 3E:
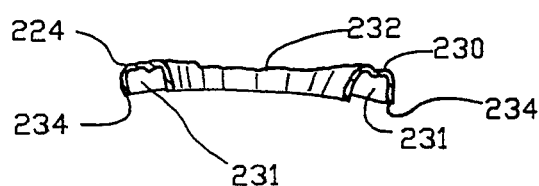

FIG. 3E is a fifth step in the second embodiment of the present invention illustrating the removal of the stint 230 from the model 210 with the stint 230 being formed with an internal region 231 and an external region 232. The stint 230 is trimmed by a cutting tool (not shown) to terminate at 234 proximate the junction 236 of the teeth 222 and the gingival tissue 238 commonly referred to as the tooth gingival margin.

Figure 3F:
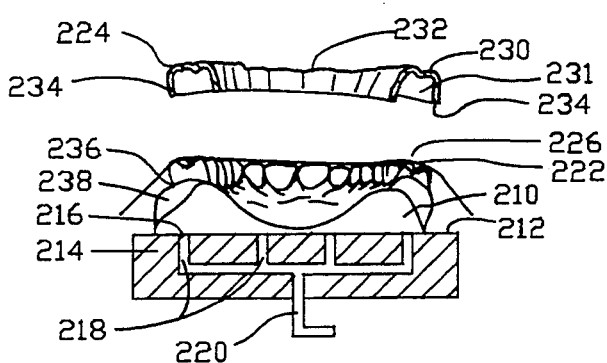

FIG. 3F is a sixth step in the second embodiment of the present invention illustrating the positioning of a retaining material 226 upon the model 210. In this embodiment, the retaining material 226 is shown as a thin sheet of fibrous absorbent retaining material. Preferably, the fibrous absorbent retaining material 226 has a thickness of 0.001" to 0.005". The retaining material 226 may be optionally moistened for facilitating the formation thereof as will be described hereinafter.

Figure 3G:
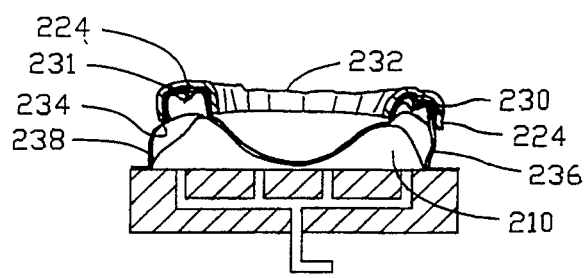

FIG. 3G is a seventh step in the second embodiment of the present invention illustrating the forming of the retaining material 226 upon the model 210 by the stint 230. The formed stint 230 is placed upon the model 210 with the retaining material 226 interposed therebetween. The formed stint 230 and the model 210 form the retaining material into the shape of the internal region 231. The retaining material 226 is frictionally retained within the internal region 231 of the stint 230. If desired, an adhesive may be applied to the stint 230 and/or the retaining material 226 prior to placing the stint 230 upon the model 210 with the retaining material 226 interposed therebetween for permanently securing the retaining material 226 to the stint 230.

Figure 3H:
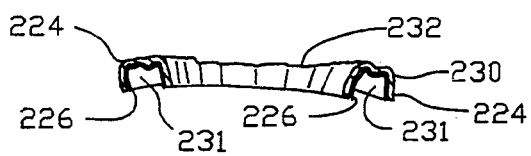

FIG. 3H is an eighth step in the second embodiment of the present invention illustrating the trimming of the retaining material 226 to the stint 230. The retaining material 226 is trimmed by a cutting tool (not shown) adjacent the termination 234 of the stint 230.

Figure 3I:
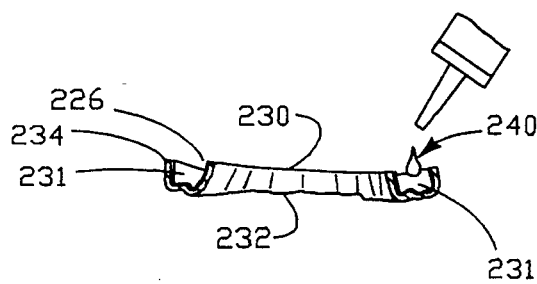
FIG. 3I is a ninth step in the second embodiment of the present invention illustrating the introduction of the active agent within the retaining material within the stint.

FIG. 3I is a ninth step in the second embodiment of the present invention illustrating the introduction of the active agent 240 within the internal region 231 of the stint 230. The presence of the absorbent retaining material 226 in the internal region 231 of the stint 230 allows the active agent 240 to be absorbed within the retaining material 226 to retain the active agent 240 in close proximity to the teeth 222 of the patient to provide superior results relative to the prior art.

Figure 4:
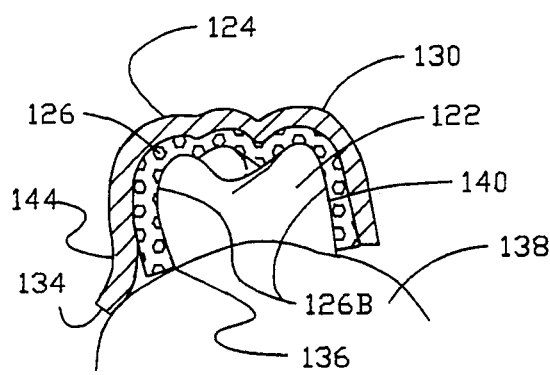
FIG. 4 is a sectional view of the improved stint shown in FIGS. 2A-2F disposed upon a tooth of a patient.

FIG. 4 is an enlarged sectional view of the first embodiment of the improved stint 130 shown in FIGS. 2A-2F containing the active agent 140 disposed upon a tooth 122 of the patient. The termination 134 of the stint 130 approximates the gingiva 138 to retain the active agent 140 within the internal region 131 of the stint 130.

In the first embodiment shown in FIG. 4, the retaining material 126 not only aids in the retention of the active agent but also allows the ingress and egress of oxygen to the gingiva tissue 138. Accordingly, the stint 130 of the present invention may utilize an overlap 144 of the gingiva tissue 138 by as much as 3.0 millimeters. The overlap 144 of the gingiva tissue 138 allowed by the stint 130 of the present invention provides a superior adaptation for treatment of the gingival tissue over the prior art stint 30.

The presence of the retaining material 126 and the natural resiliency of the closed cell foam makes the stint 130 more comfortable to wear for the patient. Accordingly, the patient will be inclined to wear the stint 130 of the present invention for a longer period of time relative to the prior art stint 30 thus producing faster results relative to the prior art stint 30. Additionally, the non uniform surface of the closed cell foam enhances the retention of the active agent within the stint 130.

Figure 5:
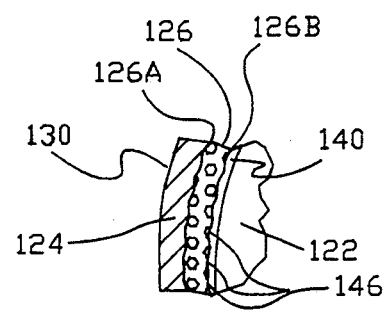
FIG. 5 is an enlarged sectional view of the improved stint shown in FIGS. 2A-2F disposed upon a tooth of a patient.

FIG. 5 is an enlarged sectional view of a portion of the improved stint 130 shown in FIG. 4. The foam retaining material 126 has a plurality of baffles or indentations 146 to trap and hold the active agent 140 against the tooth 122 to provide a superior performance relative to the prior art. Although the prior art stint 30 was closely fitted to the surface of the teeth 22, the active agent 40 within the stint 30 tended to wash out of the stint 30. In addition, areas where the prior art stint closely fitted against the surface of the tooth prevented the active agent from treating that portion of the tooth. This disadvantage of the prior art stint caused undesired irregular treatment of the tooth.

In the first embodiment of the invention, the plurality of baffles 146 of the retaining material 126, retains the active agent 140 within the stint 130 and impedes the washing away of the active agent 140 from the stint 130. Accordingly, the active agent 140 stays in contact with the surface of the teeth 122 of the patient thus providing superior results with the same active agent 140. Furthermore, the baffles 146 maintain the active agent uniformly against the surface of the tooth to provide a uniform treatment.

Figure 6:
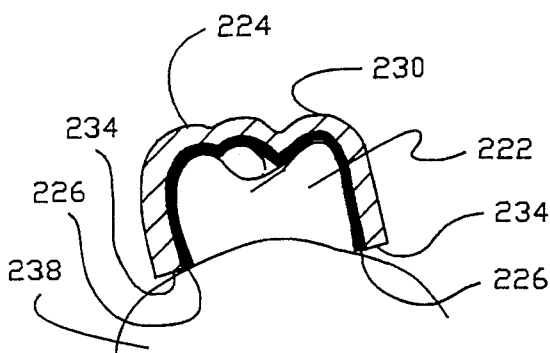
FIG. 6 is a sectional view of the improved stint shown in FIGS. 3A-3I disposed upon a tooth of a patient.

FIG. 6 is an enlarged sectional view of the second embodiment of the improved stint 230 shown in FIGS. 3A-3I disposed upon a tooth 222 of a patient. The termination 234 of the stint 230 ends with the gingiva 238 to retain the active agent 240 within the internal region 231 of the stint 230. In this example, the retaining material 226 is uniformly disposed about the entire external surface of the tooth 222 of the patient.

Figure 7:
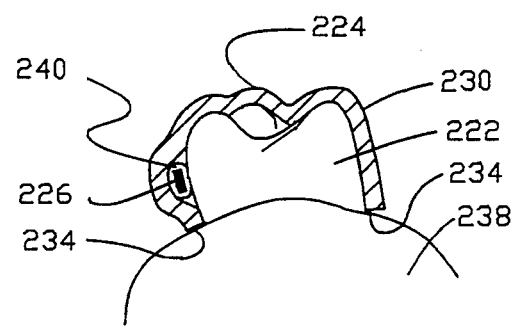
FIG. 7 is a sectional view of the improved stint shown in FIGS. 3A-3I disposed upon a tooth of a patient with the retaining material being preferentially inserted into a selected portion of the stint to preferentially treat a selected portion of the tooth.

FIG. 7 is an enlarged sectional view of the second embodiment of the improved stint 230 shown in FIGS. 3A-3I disposed upon a tooth 222 of a patient with the retaining material 226 being preferentially inserted into a selected portion of the stint 230 to preferentially treat a selected portion of the tooth 222. In some instances, only a portion of the tooth 222 requires the treatment by the active agent 240. Accordingly, the retaining material 226 may be preferentially inserted into a selected portion of the stint 230. For example, the selected portion of the tooth 222 is first identified and the retaining material 226 is temporarily affixed by means such as a temporary adhesive to the model 210 to cover the selected portion of the tooth 222. Thereafter, the stint 230 is molded in the manner shown in FIGS. 3A-3E. The retaining material 226 may then be removed from the model 210 and may be affixed by means such as a permanent adhesive to the selected portion of the stint 230. When the active agent is applied to the retaining material 126 in the selected portion of the stint 230, the retaining material 126 is in register with the selected portion of the stint 230 for preferentially treating the selected portion of the tooth 222. This advantage of the second embodiment of the improved stint enables the selective treatment of a single tooth or a selected portion or portions of a single tooth or a plurality of selected teeth.

FIGS. 8A-8H are rear views partially in section of a third embodiment of the present invention illustrating the process of treating a tooth with a stint.

Figure 8A:
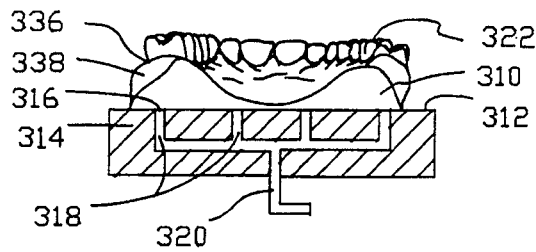
FIGS. 8A-8H are rear views partially in section of a third embodiment of the present invention illustrating the process of treating a tooth with a stint with FIGS. 8A-8H illustrating the individual process steps.

FIG. 8A is a first step in the third embodiment of the present invention illustrating the positioning of a model 310 upon an upper surface 312 of a vacuum table 314 having a plurality of apertures 316 which are connected by conduits 318 to a manifold 320.

Figure 8B:
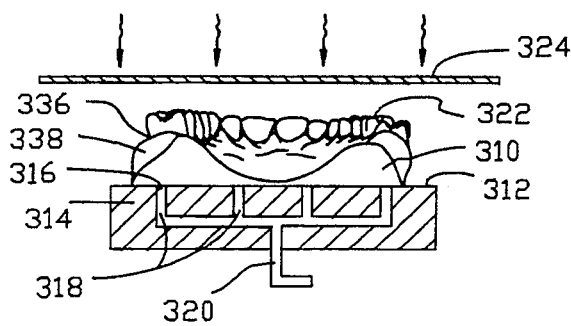

FIG. 8B is a second step in the third embodiment of the present invention illustrating the heating of a plastic material 324 for forming the stint 330.

Figure 8C:
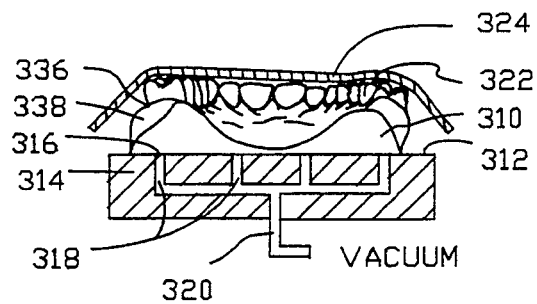

FIG. 8C is a third step in the third embodiment of the present invention illustrating the positioning of the heated plastic material 324 upon the model 310. The heated sheet of plastic material 324 begins to form into the contour of the model 310 by the action of gravity.

Figure 8D:
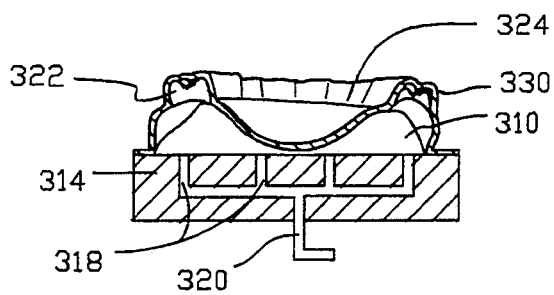

FIG. 8D is a fourth step in the third embodiment of the present invention illustrating the application of a vacuum to the manifold 320 for vacuum forming of the heated plastic material 324 upon the model 310 to form the stint 330. The vacuum forming process forms the heated plastic material 324 into an exact reproduction of the outer surfaces of the teeth 322 of the patient.

Figure 8E:
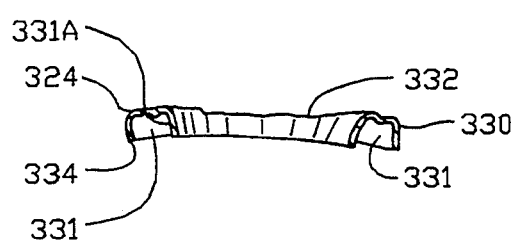

FIG. 8E is a fifth step in the third embodiment of the present invention illustrating the removal of the vacuum formed stint 330 from the model 310. The stint 330 is formed with an internal region 331 defined by an internal surface 331A and an external region 332. The stint 330 is trimmed by a cutting tool (not shown) such as crown scissors to terminate at 334 proximate the junction 336 of the teeth 322 and the gingival tissue 338 commonly referred to as the tooth gingival margin.

Figure 8F:
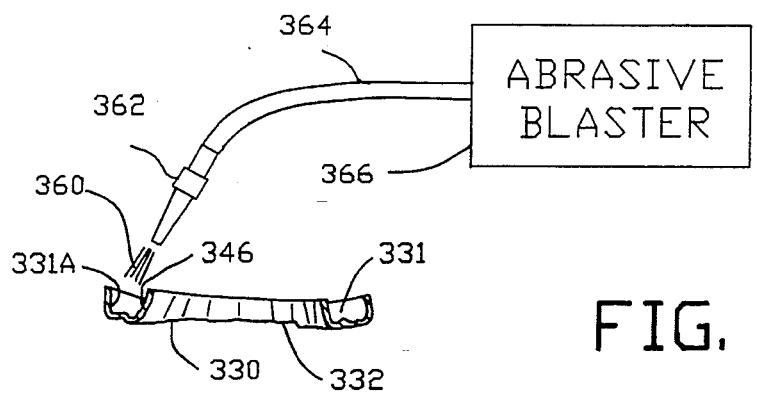

FIG. 8F is a sixth step in the third embodiment of the present invention illustrating the abrading of the internal surface 331A of the internal region 331 of the stint 310. Preferably, the abrading of the internal surface 331A is accomplished by projecting an abrasive 360 onto the internal surface 331A of the stint 330 after the completion of the molding of the stint 330. In this embodiment, the abrasive 360 is projected from a nozzle 362 connected by a hose 364 to an abrasive blaster 366. The abrasive blaster 366 projects the abrasive 360 at a high velocity from the nozzle 362 onto the internal surface 331A of the stint 330 to create the indentations 346 thereby. Although many types of abrasive may be used with this process, a high quality sand product is suitable for use with the present invention.

Figure 8G:
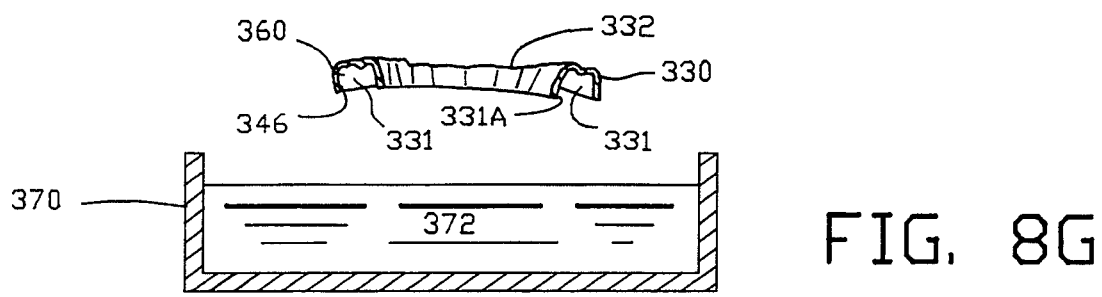

FIG. 8G is a seventh step in the third embodiment of the present invention illustrating the cleaning of an internal region 331 of the stint 330 to remove any remaining abrasive 360. In this embodiment, the stint 330 is immersed in an ultrasonic cleaning bath 370 having a liquid cleaning material 372. Alternatively, the stint 330 may be cleaned by immersion and brushing in a conventional cleaning bath or a conventional spray cleaning process.

Figure 8H:
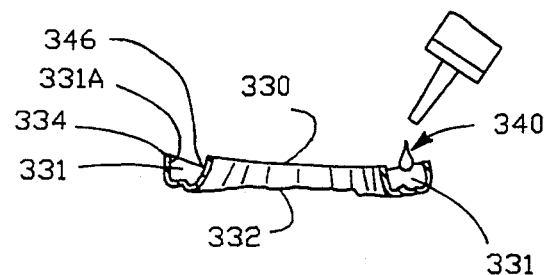
Figure 9:
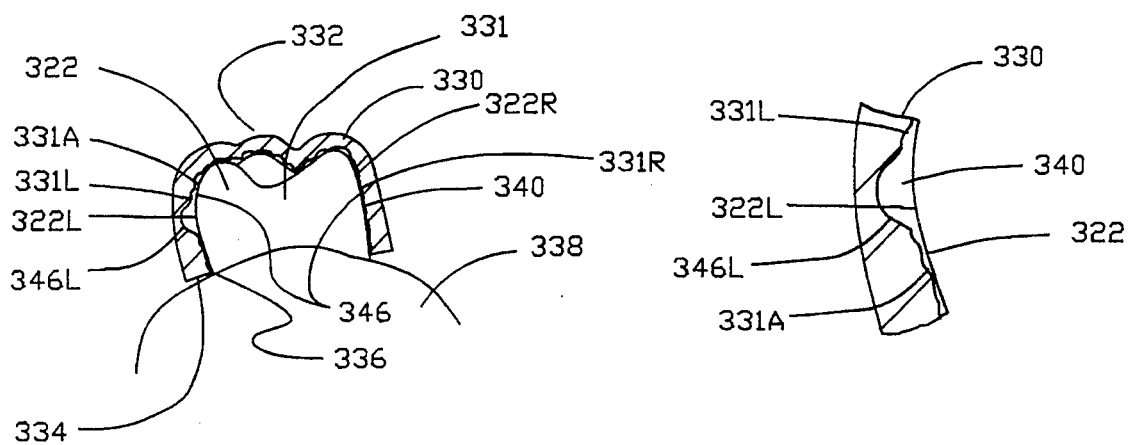
FIG. 9 is a sectional view of the improved stint shown in FIG. 8H disposed upon a tooth of a patient.

FIG. 8H is an eighth step in the third embodiment of the present invention illustrating the introduction of the active agent 340 within the internal region 331 of the stint 330. Thereafter, the stint 330 containing the active agent 340 is applied upon the teeth 322 of the patient as shown in FIG. 9. The termination 334 of the stint 330 seals with the gingiva 338 to retain the active agent 340 within the internal region 331 of the stint 330. The presence of the indentations 346 on the internal surface 331A of the internal region 331 of the stint 330 aids in retaining the active agent 340 within the stint 330 and in close proximity to the teeth 322 of the patient to provide superior results. The non-uniform internal surface 331A due to the indentations or baffles 346 within the internal region 331 of the stint 330 retains the active agent 340 within the internal region 331 of the stint 330.

Figure 10:
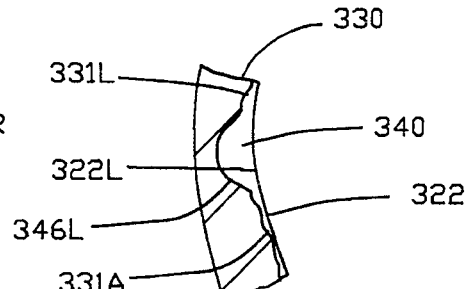
FIG. 10 is an enlarged view of a portion of FIG. 9.

FIG. 9 is an enlarged sectional view of a portion of the improved stint 330 shown in FIG. 8 whereas FIG. 10 is a further enlarged sectional view of FIG. 9. The indentations 346 on the internal surface 331A provides a plurality of baffles to trap and hold the active agent 340 against the tooth 322 to provide a superior performance relative to the prior art. The plurality of indentations 346 formed on the inside surface 331A retains the active agent 340 within the stint 330 and impedes the washing away of the active agent 340 from the stint 330.

The plurality of indentations 346 disposed on a right side 331R of the internal surface 331A of the stint 330 are uniformly disposed about a right side 222R of the tooth 222 of the patient. Accordingly, the active agent 340 stays in uniform contact with the right side surface 222R of the teeth 322.

As best shown in FIG. 9, the improved stint 310 enables the selective treatment of a single tooth or a selected portion or portions of a single tooth or a plurality of teeth. An indentation 346L disposed on a left side 331L of the internal surface 331A of the stint 330 is preferentially enlarged relative to the indentations 346 disposed on the right side 331R of the internal surface 331A of the stint 330.

When only a selected portion 322S of the tooth 322 requires the treatment by the active agent 340, a selected portion of the internal surface 331A of the stint 330 is formed with the preferentially enlarged indentation 346L. The preferentially enlarged indentation 346L is formed by an operator to be adjacent the selected portion 322S of the tooth 322. The enlarged indentation 346L may be created by directing the nozzle 362 of the abrasive blaster 366. Preferential abrasive blasting by the abrasive blaster 366 will produce a preferential enlarged indentation 346L in the internal surface 331A of the stint 330. The enlarged indentation 346L will retain a greater amount of the active agent 340 to apply a faster treatment to the selected portion 322S of the tooth 322.

When the active agent is applied to the internal portion 331 of the stint 330, the enlarged indentation 346L is in register with the selected portion 322S of the tooth 322 for preferentially treating the selected portion 322S of the tooth 322.

The apparatus and method of the present invention may be utilized in various treatments of a tooth or other oral structures including the treatment for whitening teeth, fluoride treatment, as well as the application of antibiotics, antihistamines, topical anesthetics, chemotherapy, steroids, astringents, antiseptics, anti-inflammatory and the like.

In periodontal procedures such as root planing and deep scaling, the stint can be placed in the mouth of the patient to apply a topical anesthetic several minutes prior to the procedure thereby reducing the discomfort or pain to the patient. The improved stint may be used to apply a fluoride treatment for reducing post operative complications, for remineralizing the damaged areas of the root surfaces as well as insulating the surfaces to prevent sensitivity.

The improved stint of the present invention may be used in antihistamine procedures to reduce topical inflammation of periodontal structures, fluoride treatment such as the treatment of decalcification, radiation therapy and rampant caries, acute sensitive and xerostomia.

In one example, the apparatus and method of the present invention has been successfully used in a tooth whitening process. A solution of 11% perhydrol urea in a base solution of glycerine (99.9% water free) with a base stabilizer of 0.015% potassium citrate has been found to be effective as a tooth whitening agent.

The stint may be formed from a variety of materials such as polymers, copolymers, composites and the like. Stints have been successfully formed from 0.020" to 0.040" polycarbonate coping material. The polycarbonate material has been found to be more comfortable for the patient than harder material such as acrylics and the like. Furthermore, the resiliency of the polycarbonate material does not produce undesired orthodontic movement.

The foam retaining material shown in FIGS. 2A–2F may be selected from a variety of materials as should be apparent to those skilled in the art. However, superior results have been achieved using low density foam polyethylene in a thickness range of 1/32" to 3/32". In a similar manner, the fibrous retaining material shown in FIGS. 3A–3I may be selected from a variety of materials having a thickness of 0.001" to 0.005". For example, conventional filters for drip coffee makers have been found to be an effective fibrous retaining material. Other suitable materials include medical grade milioliform filter material.

The apparatus and method of the present invention when applied to a tooth whitening process has been found to produce faster results with less discomfort for the patient than the prior art process shown in FIGS. 1A–1F.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An improved method of whitening a tooth with an active agent, comprising the steps of:
making a model of the tooth;
molding a stint to define an internal region and an external region with the internal region overlaying the tooth and the adjacent gingiva tissue;

trimming the stint to overlay only the tooth and to terminate at the juncture of the tooth and the gingiva tissue;

abrading the internal region of the stint to form indentations within the internal region of the stint;

introducing the active agent to brighten the tooth into the indentations; and applying the stint containing the active agent upon the tooth.

2. An improved method of treating a tooth with an active agent as set forth in claim 1, wherein the step of molding the stint to overlay the tooth includes vacuum forming a sheet of plastic material over the model of the tooth.

3. An improved method of treating a tooth with an active agent as set forth in claim 1 wherein the step of molding the stint to overlay the tooth includes molding the stint to overlay a plurality of teeth.

4. An improved method of treating a tooth with an active agent as set forth in claim 1, wherein the step of forming indentations within the internal region of the stint includes projecting an abrasive onto an internal surface of the stint to create the indentations thereby.

5. An improved method of treating a tooth with an active agent as set forth in claim 1, wherein the step of forming indentations within the internal region of the stint includes projecting a high velocity abrasive onto an internal surface of the stint to create the indentations thereby.

6. An improved method of treating a tooth with an active agent as set forth in claim 1, wherein the step of forming indentations within the internal region of the stint includes projecting a high velocity abrasive onto an internal surface of the stint to create the indentations thereby after the completion of the molding of the stint.

7. An improved method of treating a tooth with an active agent as set forth in claim 1, wherein the step of introducing the active agent into the indentations includes at least partially filling the internal region of the stint with the active agent to be retained by the indentations and to provide excess quantities of the active agent.

8. An improved method of treating a tooth with an active agent as set forth in claim 1, wherein the step of applying the stint and the active agent upon the tooth includes applying the stint upon the tooth with the stint at least partially sealing the internal region from the external region of the stint proximate the termination of the stint at the juncture of the tooth and the gingiva tissue.

9. An improved method of treating a tooth with an active agent as set forth in claim 1, wherein the step of forming indentations within the internal region of the stint includes preferentially forming indentations into selected portions of an internal surface of the stint to preferentially treat a portion of the tooth adjacent the indentations.

10. An improved method of treating a tooth with an active agent as set forth in claim 1, wherein the active agent comprises a bleaching agent comprising a solution of 11% perhydrol urea in a base solution of glycerine with a base stabilizer of 0.015% potassium citrate.

11. An improved method of treating a tooth with an active agent, comprising the steps of:
making a model of the tooth;
molding a stint to define an internal region to overlay the tooth;
forming one or more indentations within the internal region of the stint by abrading an internal surface of the stint to create said one or more indentations thereby;
introducing the active agent into the indentations of the stint; and
applying the stint containing the active agent upon the tooth.

12. An improved method of treating a tooth with an active agent as set forth in claim 11, wherein the step of molding the stint to overlay the tooth includes vacuum forming a sheet of plastic material over the model of the tooth.

13. An improved method of treating a tooth with an active agent as set forth in claim 11, wherein the step of molding the stint to overlay the tooth includes molding the stint to overlay a plurality of teeth.

14. An improved method of treating a tooth with an active agent as set forth in claim 11, including the step of trimming the stint to terminate at the juncture of the tooth and the gingiva tissue.

15. An improved method of treating a tooth with an active agent as set forth in claim 11, wherein the step of introducing the active agent into the indentations includes at least partially filling the internal region of the stint with the active agent to be retained by the indentations and to provide excess quantities of the active agent.

16. An improved method of treating a tooth with an active agent as set forth in claim 11, wherein the step of applying the stint and the active agent upon the tooth includes applying the stint upon the tooth with the stint at least partially sealing the internal region from the external region of the stint proximate the termination of the stint at the juncture of the tooth and the gingiva tissue.

17. An improved method of treating a tooth with an active agent as set forth in claim 11, wherein the step of forming indentations within the internal region of the stint includes preferentially forming indentations into selected portions of an internal surface of the stint to preferentially treat a portion of the tooth adjacent the indentations.

18. An improved method of treating a tooth with an active agent as set forth in claim 11, wherein the active agent comprises a bleaching agent comprising a solution of 11% perhydrol urea in a base solution of glycerine with a base stabilizer of 0.015% potassium citrate.

19. An improved method of treating a tooth with an active agent, comprising the steps of:
making a model of the tooth;
molding a stint to define an internal region to overlay the tooth;
forming One or more indentations within the internal region of the stint by projecting an abrasive onto an internal surface of the stink to create said one or more indentations thereby;
introducing the active agent into the indentations of the stint; and
applying the stint containing the active agent upon the tooth.

20. An improved method of treating a tooth with an active agent as set forth in claim 19, wherein the step of molding the stint to overlay the tooth includes vacuum forming a sheet of plastic material over the model of the tooth.

21. An improved method of treating a tooth with an active agent as set forth in claim 19, wherein the step of molding the stint to overlay the tooth includes molding the stint to overlay a plurality of teeth.

22. An improved method of treating a tooth with an active agent as set forth in claim 19, including the step of trimming the stint to terminate at the juncture of the tooth and the gingiva tissue.

23. An improved method of treating a tooth with an active agent as set forth in claim 19, wherein the step of introducing the active agent into the indentations includes at least partially filling the internal region of the stint with the active agent to be retained by the indentations and to provide excess quantities of the active agent.

24. An improved method of treating a tooth with an active agent as set forth in claim 19, wherein the step of applying the stint and the active agent upon the tooth includes applying the stint upon the tooth with the stint at least partially sealing the internal region from the external region of the stint proximate the termination of the stint at the juncture of the tooth and the gingiva tissue.

25. An improved method of treating a tooth with an active agent as set forth in claim 19, wherein the step of forming indentations within the internal region of the stint includes preferentially forming indentations into selected portions of an internal surface of the stint to preferentially treat a portion of the tooth adjacent the indentations.

26. An improved method of treating a tooth with an active agent as set forth in claim 19, wherein the active agent comprises a bleaching agent comprising a solution of 11% perhydrol urea in a base solution of glycerine with a base stabilizer of 0.015% potassium citrate.

27. An improved method of treating a tooth with an active agent, comprising the steps of:
  making a model of the tooth;
  molding a stint to define an internal region to overlay the tooth;
  forming one or more indentations within the internal region of the stint by projecting a high velocity abrasive onto an internal surface of the stint to create said one or more indentations thereby;
  introducing the active agent into the indentations of the stint; and
  applying the stint containing the active agent upon the tooth.

28. An improved method of treating a tooth with an active agent as set forth in claim 27, wherein the step of molding the stint to overlay the tooth includes vacuum forming a sheet of plastic material over the model of the tooth.

29. An improved method of treating a tooth with an active agent as set forth in claim 27, wherein the step of molding the stint to overlay the tooth includes molding the stint to overlay a plurality of teeth.

30. An improved method of treating a tooth with an active agent as set forth in claim 27, including the step of trimming the stint to terminate at the juncture of the tooth and the gingiva tissue.

31. An improved method of treating a tooth with an active agent as set forth in claim 27, wherein the step of introducing the active agent into the indentations includes at least partially filling the internal region of the stint with the active agent to be retained by the indentations and to provide excess quantities of the active agent.

32. An improved method of treating a tooth with an active agent as set forth in claim 27, wherein the step of applying the stint and the active agent upon the tooth includes applying the stint upon the tooth with the stint at least partially sealing the internal region from the external region of the stint proximate the termination of the stint at the juncture of the tooth and the gingiva tissue.

33. An improved method of treating a tooth with an active agent as set forth in claim 27, wherein the step of forming indentations within the internal region of the stint includes preferentially forming indentations into selected portions of an internal surface of the stint to preferentially treat a portion of the tooth adjacent the indentations.

34. An improved method of treating a tooth with an active agent as set forth in claim 27, wherein the active agent comprises a bleaching agent comprising a solution of 11% perhydrol urea in a base solution of glycerine with a base stabilizer of 0.015% potassium citrate.

35. An improved method of treating a tooth with an active agent, comprising the steps of:
  making a model of the tooth;
  molding a stint to define an internal region to overlay the tooth;
  forming one or more indentations within the internal region of the stint by projecting a high velocity abrasive onto an internal surface of the stint to create the indentations thereby after the completion of the molding of the stint;
  introducing the active agent into the indentations of the stint; and
  applying the stint containing the active agent upon the tooth.

36. An improved method of treating a tooth with an active agent as set forth in claim 35, wherein the step of molding the stint to overlay the tooth includes vacuum forming a sheet of plastic material over the model of the tooth.

37. An improved method of treating a tooth with an active agent as set forth in claim 35, wherein the step of molding the stint to overlay the tooth includes molding the stint to overlay a plurality of teeth.

38. An improved method of treating a tooth with an active agent as set forth in claim 35, including the step of trimming the stint to terminate at the juncture of the tooth and the gingiva tissue.

39. An improved method of treating a tooth with an active agent as set forth in claim 36, wherein the step of introducing the active agent into the indentations includes at least partially filling the internal region of the stint with the active agent to be retained by the indentations and to provide excess quantities of the active agent.

40. An improved method of treating a tooth with an active agent as set forth in claim 35, wherein the step of applying the stint and the active agent upon the tooth includes applying the stint upon the tooth with the stint at least partially sealing the internal region from the external region of the stint proximate the termination of the stint at the juncture of the tooth and the gingiva tissue.

41. An improved method of treating a tooth with an active agent as set forth in claim 35, wherein the step of forming indentations within the internal region of the stint includes preferentially forming indentations into selected portions of an internal surface of the stint to preferentially treat a portion of the tooth adjacent the indentations.

42. An improved method of treating a tooth with an active agent as set forth in claim 35, wherein the active agent comprises a bleaching agent comprising a solution of 11% perhydrol urea in a base solution of glycerine with a base stabilizer of 0.015% potassium citrate.

* * * * *

UNITED STATES PATENT AND TRADEMARK OFFICE
CERTIFICATE OF CORRECTION

PATENT NO. : 5,356,291

DATED : October 18, 1994

INVENTOR(S) : Daniel H. Darnell

It is certified that error appears in the above-identified patent and that said Letters Patent is hereby corrected as shown below:

In Claim 19, Column 14, line 57 of the Patent, change "stink" to --stint--.

In Claim 39, Column 16, line 43 of the Patent, change "36" to --35--.

Signed and Sealed this

Twenty-fourth Day of January, 1995

BRUCE LEHMAN

Attest:

Attesting Officer

Commissioner of Patents and Trademarks